US007566537B2

(12) United States Patent
Balasubramanian et al.

(10) Patent No.: US 7,566,537 B2
(45) Date of Patent: Jul. 28, 2009

(54) LABELLED NUCLEOTIDES

(75) Inventors: Shankar Balasubramanian, Cambridge (GB); Colin Barnes, Nr. Saffron Walden (GB); Xiaohai Liu, Nr. Saffron Walden (GB); John Milton, Nr. Saffron Walden (GB); Harold Swerdlow, Nr. Saffron Walden (GB); Xiaolin Wu, Nr. Saffron Walden (GB)

(73) Assignee: Illumina Cambridge Limited, Nr. Saffron Walden (GB)

( * ) Notice: Subject to any disclaimer, the term of this patent is extended or adjusted under 35 U.S.C. 154(b) by 152 days.

(21) Appl. No.: 11/301,578

(22) Filed: Dec. 13, 2005

(65) Prior Publication Data

US 2006/0188901 A1    Aug. 24, 2006

Related U.S. Application Data

(62) Division of application No. 10/227,131, filed on Aug. 23, 2002, now Pat. No. 7,057,026.

(30) Foreign Application Priority Data

Dec. 4, 2001    (GB) .................. 0129012.1

(51) Int. Cl.
  C12Q 1/68    (2006.01)
  C12P 19/34   (2006.01)
  C12M 1/34    (2006.01)
  C07H 21/00   (2006.01)
(52) U.S. Cl. .............. 435/6; 435/91.1; 435/287.2; 536/23.1
(58) Field of Classification Search ............. 536/23.1; 435/6, 91.1, 287.2
See application file for complete search history.

(56) References Cited

U.S. PATENT DOCUMENTS

| 4,711,955 | A | 12/1987 | Ward et al. |
| 4,772,691 | A | 9/1988 | Herman |
| 4,824,775 | A | 4/1989 | Dattagupta et al. |
| 4,863,849 | A | 9/1989 | Melamede |
| 5,118,605 | A | 6/1992 | Urdea |
| 5,174,962 | A | 12/1992 | Brennan |
| 5,175,269 | A | 12/1992 | Stavrianopoulos |
| 5,302,509 | A | 4/1994 | Cheeseman |
| 5,328,824 | A | 7/1994 | Ward et al. |
| 5,436,143 | A | 7/1995 | Hyman |
| 5,449,767 | A | 9/1995 | Ward et al. |
| 5,476,928 | A | 12/1995 | Ward et al. |
| 5,516,664 | A | 5/1996 | Hyman |

(Continued)

FOREIGN PATENT DOCUMENTS

DE    41 41 178    6/1993

(Continued)

OTHER PUBLICATIONS

Greene et al. (Protective Groups in Organic Chemistry, John Wiley & Sons: New York, 1991, pp. 42-45, and 417.*

(Continued)

*Primary Examiner*—Jezia Riley
(74) *Attorney, Agent, or Firm*—Klauber & Jackson LLC

(57) ABSTRACT

Nucleosides and nucleotides are disclosed that are linked to detectable labels via a cleavable linker group.

15 Claims, 6 Drawing Sheets

Uridine C5-linker

Cytidine C5-linker

N7 Deazaadenosine C7-linker

N7 Deazaguanosine C7-linker

Adenosine N6-linker

Cytidine N4-linker where $R_1$ and $R_2$, which may be the same or different, are each selected from H, OH, or any group which can be transformed into an OH. Suitable groups for $R_1$ and $R_2$ are described in Figure 3

X = H, phosphate, diphosphate or triphosphate

Guanosine N2-linker

U.S. PATENT DOCUMENTS

| | | | |
|---|---|---|---|
| 5,534,424 | A | 7/1996 | Uhlen et al. |
| 5,547,839 | A | 8/1996 | Dower et al. |
| 5,547,859 | A | 8/1996 | Goodman et al. |
| 5,602,000 | A | 2/1997 | Hyman |
| 5,763,594 | A | 6/1998 | Hiatt et al. |
| 5,770,367 | A | 6/1998 | Southern et al. |
| 5,798,210 | A | 8/1998 | Canard et al. |
| 5,808,045 | A | 9/1998 | Hiatt et al. |
| 5,821,356 | A | 10/1998 | Khan et al. |
| 5,849,542 | A | 12/1998 | Reeve et al. |
| 5,872,244 | A | 2/1999 | Hiatt et al. |
| 5,885,775 | A | 3/1999 | Haff et al. |
| 6,001,566 | A | 12/1999 | Canard et al. |
| 6,008,379 | A | 12/1999 | Benson et al. |
| 6,046,005 | A | 4/2000 | Ju et al. |
| 6,074,823 | A | 6/2000 | Koster |
| 6,087,095 | A | 7/2000 | Rosenthal et al. |
| 6,136,543 | A | 10/2000 | Anazawa et al. |
| 6,214,987 | B1 | 4/2001 | Hiatt et al. |
| 6,218,118 | B1 | 4/2001 | Sampson et al. |
| 6,218,530 | B1 | 4/2001 | Rothschild et al. |
| 6,232,465 | B1 | 5/2001 | Hiatt et al. |
| 6,242,193 | B1 | 6/2001 | Anazawa et al. |
| 6,255,475 | B1 | 7/2001 | Kwiatkowski |
| 6,287,821 | B1 | 9/2001 | Shi et al. |
| 6,309,836 | B1 | 10/2001 | Kwiatkowski |
| 6,312,893 | B1 | 11/2001 | Van Ness et al. |
| 6,380,378 | B1 | 4/2002 | Kitamura et al. |
| 6,524,829 | B1 | 2/2003 | Seeger |
| 6,613,508 | B1 | 9/2003 | Ness et al. |
| 6,639,088 | B2 | 10/2003 | Kwiatkowski |
| 6,664,079 | B2 | 12/2003 | Ju et al. |
| 6,780,591 | B2 | 8/2004 | Williams et al. |
| 6,787,308 | B2 | 9/2004 | Balasubramanian et al. |
| 6,911,345 | B2 | 6/2005 | Quake et al. |
| 6,982,146 | B1 | 1/2006 | Schneider et al. |
| 7,037,687 | B2 | 5/2006 | Williams et al. |
| 7,056,666 | B2 | 6/2006 | Dower et al. |
| 7,057,026 | B2 | 6/2006 | Barnes et al. |
| 7,057,031 | B2 | 6/2006 | Olejnik et al. |
| 7,074,597 | B2 | 7/2006 | Ju |
| 7,078,499 | B2 | 7/2006 | Odedra et al. |
| 7,105,300 | B2 | 9/2006 | Parce et al. |
| 7,414,116 | B2 | 8/2008 | Milton et al. |
| 7,427,673 | B2 | 9/2008 | Balasubramanian et al. |
| 7,459,275 | B2 | 12/2008 | Dower et al. |
| 2003/0008285 | A1 | 1/2003 | Fischer |
| 2003/0186256 | A1 | 10/2003 | Fischer |
| 2004/0014096 | A1 | 1/2004 | Anderson et al. |
| 2004/0096825 | A1 | 5/2004 | Chenna et al. |
| 2007/0166705 | A1 | 7/2007 | Milton et al. |

FOREIGN PATENT DOCUMENTS

| | | |
|---|---|---|
| EP | 0 992 511 | 4/2000 |
| EP | 1182267 | 2/2002 |
| EP | 1291354 | 3/2003 |
| EP | 0808320 | 4/2003 |
| EP | 1337541 | 3/2007 |
| EP | 1218391 | 4/2007 |
| EP | 1790736 | 5/2007 |
| WO | WO 89/09282 | 10/1989 |
| WO | WO 90/13666 | 11/1990 |
| WO | WO 91/06678 * | 5/1991 |
| WO | WO 92/10587 | 6/1992 |
| WO | WO 93/05183 | 3/1993 |
| WO | WO 93/21340 | 10/1993 |
| WO | WO 94/14972 | 7/1994 |
| WO | WO 96/07669 | 3/1996 |
| WO | WO 96/23807 | 8/1996 |
| WO | WO 96/27025 | 9/1996 |
| WO | WO 98/30720 | 7/1998 |
| WO | WO 99/05315 | 2/1999 |
| WO | WO 99/57321 | 11/1999 |
| WO | WO 00/02895 | 1/2000 |
| WO | WO 00/06770 | 2/2000 |
| WO | WO 00/15844 | 3/2000 |
| WO | WO 00/18956 | 4/2000 |
| WO | WO 00/21974 | 4/2000 |
| WO | WO 00/50642 | 8/2000 |
| WO | WO 00/53805 | 9/2000 |
| WO | WO 00/53812 | 9/2000 |
| WO | WO 00/70073 | 11/2000 |
| WO | WO 01/16375 | 3/2001 |
| WO | WO 01/23610 | 4/2001 |
| WO | WO 01/25247 | 4/2001 |
| WO | WO 01/32930 | 5/2001 |
| WO | WO 01/57248 | 8/2001 |
| WO | WO 01/57249 | 8/2001 |
| WO | WO 01/92284 | 12/2001 |
| WO | WO 02/02813 | 1/2002 |
| WO | WO 02/22833 | 3/2002 |
| WO | WO 02/29003 | 4/2002 |
| WO | WO 02/072892 | 9/2002 |
| WO | WO 02/079519 | 10/2002 |
| WO | WO 02/088381 | 11/2002 |
| WO | WO 02/088382 | 11/2002 |
| WO | WO 03/002767 | 1/2003 |
| WO | WO 03/020968 | 3/2003 |
| WO | WO 03/048178 | 6/2003 |
| WO | WO 03/048387 | 6/2003 |
| WO | WO 03/085135 | 10/2003 |
| WO | WO 2004/007773 | 1/2004 |
| WO | WO 2004/018493 | 3/2004 |
| WO | WO 2004/018497 | 3/2004 |
| WO | WO 2005/084367 | 9/2005 |

OTHER PUBLICATIONS

Canard et al., DNA polymerase flourescent substrates with reversible 3'-tags, Gene, 148: 1-6 (1994).

Metzker et al., Termination of DNA synthesis by novel 3'-modified-deoxyribonucleoside 5'-triphosphates, Nucleic Acids Research, 22: 4259-4267 (1994).

Hovinen et al., Synthesis of 3'-O-(ω-Aminoalkoxymethyl) thymidine 5'-Triphosphates, Terminators of DNA Synthesis that Enable 3'-Labelling, J. Chem. Soc. Perkin Trans., 1: 211-217 (1994).

Stratagene Catalog, p. 39 (1988).

Kraevskii et al., Substrate Inhibitors of DNA Biosynthesis, Translated from Molekulyamaya Biologiya [Mol. Bio. (Mosk.)]21:33-38 (1987).

Henner et al., Enzyme Action at 3' Termini of Ionizing Radiation-induced DNA Strand Breaks, The Journal of Biological Chemistry, 258:15198-15205 (1983).

J. Brunckova et al., Tetrahedron Letters, 1994, vol. 35, pp. 6619-6622.

S. Nishino et al., Heteroatom Chemistry, 1991, vol. 2, pp. 187-196.

M. Krečcmerová, Coll. Czech. Chem. Commun., 1990 vol. 55, pp. 2521-2536.

P. J. L. M. Quaedflieg et al., Tetrahedron Letters, 1992 vol. 33, pp. 3081-3084.

J. I. Yamashita et al., Chem Pharm. Bull., 1987, vol. 35, pp. 2373-2381.

S.G. Zavgorodny et al., Nucleosides, Nucleotides and Nucleic Acids, 19(10-12), 1977-1991 (2000).

U.S. Appl. No. 90/008,149, filed Aug. 4, 2006, Gitten.

U.S. Appl. No. 90/008,152, filed Aug. 3, 2006, Gitten.

Kraevskii et al., Substrate Inhibitors of DNA Biosynthesis, Molecular Biology, 21:25-29 (1987).

Kurata et al., Fluorescent quenching-based quantitative detection of specific DNA/RNA using BODIPY® FL-labeled probe or primer, Nucleic Acids Research, vol. 29, No. 6, p. e34, (2001).

WO 03/048387, Intl. Search Report Jun. 16, 2003, PCT.

WO 2004/018497, Intl. Search Report, PCT.

Ikeda et al., A Non-radioactive DNA Sequencing Method Using Biothinylated Dideoxynucleoside Triphosphates and ΔTth DNA Polymerase, 2:225-227 (1995).

Welch et al., Syntheses of Nucleosides Designed for Combinatorial DNA Sequencing, Chemistry, European Jouranl, 5:951-960 (1999).

Canard et al., Catalytic editing properties of DNA polymerases, Proc. Natl. Acad. Sci., 92:10859-10863 (1995).

Olejnik et al., Photocleavable biotin derivatives: A versatile approach for the isolation of biomolecules, Proc. Natl. Acad. Sci., 92:7590-7594 (1995).

Wada et al., 2-(Azidomethyl)benzoyl as a new protecting group in nucleosides, Tetrahedron Letters, 42:1069-1072 (2001).

Li et al., A photocleavable fluorescent nucleotide of DNA sequencing and analysis, Proc. Natl. Acad. Sci., 100:414-419 (2003).

Sarfati et al., Synthesis of fluorescent derivatives of 3'-O-(6-aminohexanoyl)-pyrimidine nucleosides 5'-triphosphates that act as DNA polymerase substrates reversibly tagged at C-3', JCS Perkin Trans, 1163-1171 (1995).

Burgess et al., An Approach to Photolabile, Fluorescent Protecting Groups, J. Org. Chem., 62:5165-5168 (1997).

Rasolonjatovo et al., 6-N- (N-Methylanthranylamido)-4-Oxo-Hexanoic Acid : A New Fluorescent Protecting Group Applicable to a New DNA Sequencing Method, Nucleosides & Nucleotides, 17:2021-2025 (1998).

Marquez et al., Selective Fluorescence Quenching of 2,3-Diazabicyclo[2.2.2]oct-2-ene by Nucteotides, Organic Letters, 5:3911-3914 (2003).

Nazarenko et al., Effect of primary and secondary structure of oligodeoxyribonucleotides on the fluorescent properties of conjugated dyes, Nucleic Acids Research, 30:2089-2095 (2002).

Kvam et al., Characterization of singlet oxygen-induced guanine residue damage after photochemical treatment of free nucleosides and DNA, Biochimica et Biophysica Acta., 1217:9-15 (1994).

Crespo-Hernandez et al., Part 1. Photochemical and Photophysical Studies of Guanine Derivatives: Intermediates Contributing to its Photodestruction Mechanism in Aqueous Solution and the Participation of the Electron Adduct, Photochemistry and Photobiology, 71(5):534-543 (2000).

Buschmann et al., Spectroscopic Study and Evaluation of Red-Absorbing Flourescent Dyes, Bioconjugate Chem., 14:195-204 (2003).

Torimura et al., Fluorescence-Quenching Phenomenon by Photoinduced Electron Transfer between a Fluorescent Dye and Nucleotide Base, Analytical Sciences, 17:155-160 (2001).

Markiewicz et al., A new method of synthesis of fluorescently labelled oligonucleotides and their application in DNA sequencing, Nucleic Acids Research, 25:3672-3680 (1997).

Maier et al., Synthesis and Properties of New Fluorescein—Labeled Oligonucleotides, Nucleosides & Nucleotides, 14:961-965 (1995).

Bergmann et al., Allyl As Internucleotide Protecting Group in DNA Synthesis to be Cleaved Off by Ammonia, Tetrahedron, 51:6971-6976 (1995).

Guibé, Allylic Protecting Groups and Their Use in a Complex Environment Part I : Allylic Protection of Alcohols, Tetrahedron, 53:13509-13556 (1997).

Guibé, Allylic Protecting Groups and Their Use in a Complex Environment Part II : Allylic Protecting Groups and their Removal through Catalytic Palladium π-Allyl Methodolgy Tetrahedron, 54:2967-3042 (1998).

Kloosterman et al., The relative stability of allyl ether, allyloxycarbonyl ester and prop-2 enylidene acetal, protective groups toward Iridium, Rhodium and Palladium catalysts, Tetrahedron Letters, 26:5045-5048 (1985).

Kitamura et al., $(P(C_6H_5)_3)CpRu+$-Catalyzed Deprotection of Allyl Carboxylic Esters, J. Org. Chem., 67:4975-4977 (2002).

Hayakawa et al., O-Allyl Protection of Guanine and Thymine Residues in Oligodeoxyribonucleotides, J. Org. Chem., 58:5551-5555 (1993).

Green et al., Protective groups in organic synthesis, John Wiley and Sons, Inc., New York, 67-74, 574-576, (1999).

Kocienski, Protecting groups, Georg Thieme Verlag, Stuttgart, 61-68, (1994).

Veeneman et al., An Efficient Approach to the Synthesis of Thymidine Derivatives Containing Phosphate-Isosteric Methylene Acetyl Linkages, Tetrahedron, 47:1547-1562 (1991).

Zavgorodny et al., 1-Alkylthioalkylation of Nucleoside Hydroxl Functions and Its Synthetic Applications: A New Versatile Method in Nucleoside Chemistry, Tetrahedron Letters, 32:7593-7596 (1991).

Seeger, Single Molecule Fluorescence: High-Performance Molecular Diagnosis and Screening, Bioforum, Git Verlag, Darmstadt, DE vol. 21 No. 4 1998, 179-185 (German text and English translation).

Kamal et al., A Mild and Rapid Regeneration of Alcohols from their Allylic Ethers by Chlorotrimethylsilane/Sodium Iodide, Tetrahedron Letters, 40:371-372 (1999).

Rao et al., Four Color FRET Dye Nucleotide Terminators for DNA Sequencing, Nucleosides, Nucleotides & Nucleic Acids, 20:673-676 (2001).

* cited by examiner

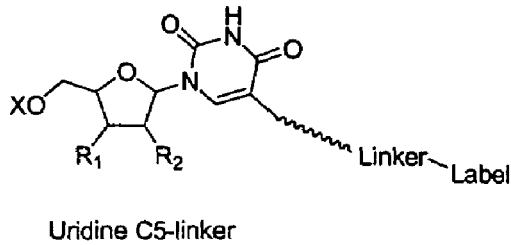

Uridine C5-linker

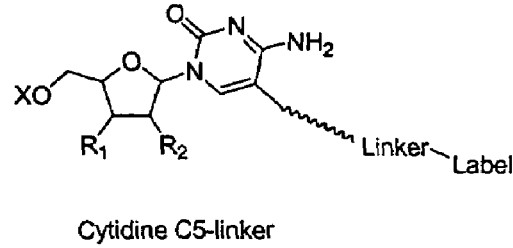

Cytidine C5-linker

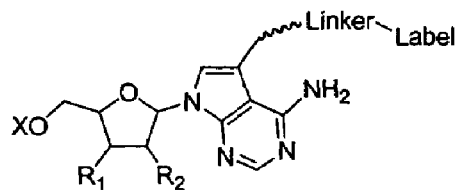

N7 Deazaadenosine C7-linker

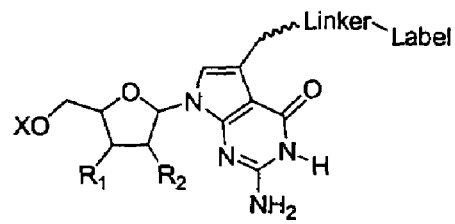

N7 Deazaguanosine C7-linker

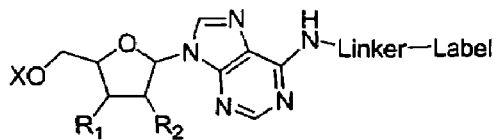

Adenosine N6-linker

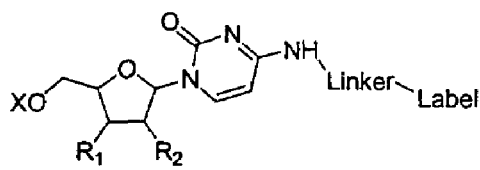

Cytidine N4-linker where $R_1$ and $R_2$, which may be the same or different, are each selected from H, OH, or any group which can be transformed into an OH. Suitable groups for $R_1$ and $R_2$ are described in Figure 3

X = H, phosphate, diphosphate or triphosphate

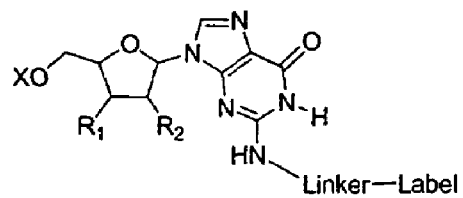

Guanosine N2-linker

Fig. 1

Label ~~~Cleavable linker~~~~~~Base

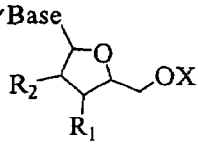

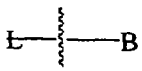

Cleavable linkers may include:

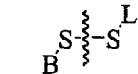

where $R_1$ and $R_2$, which may be the same or different, are each selected from H, OH, or any group which can be transformed into an OH, including a carbonyl

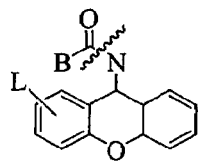

$R_1$ and $R_2$ groups may include

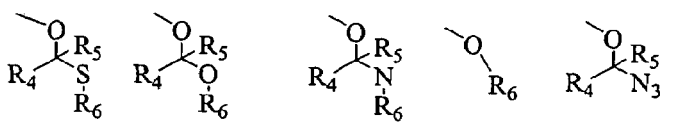

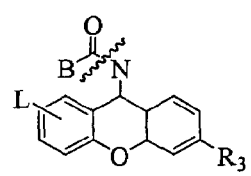

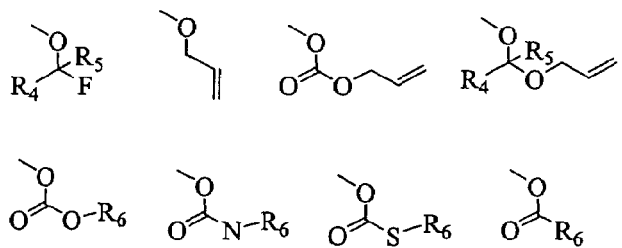

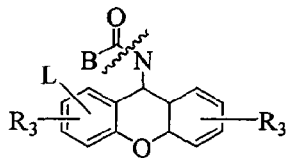

R3 represents one or more substituents independently selected from alkyl, alkoxy, amino or halogen

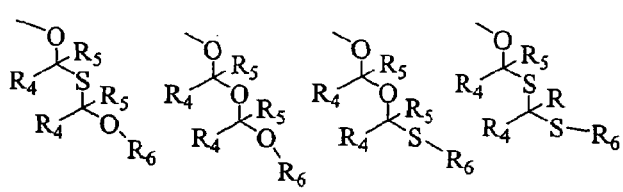

Alternatively, cleavable linkers may be constructed from any labile functionality used on the 3'-block

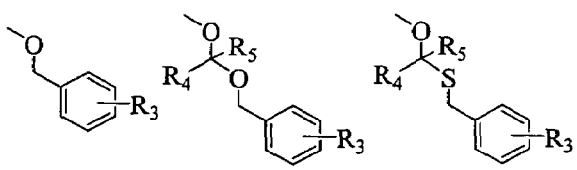

where $R_4$ is H or alkyl, $R_5$ is H or alkyl and $R_6$ is alkyl, cycloalkyl, alkenyl, cycloalkenyl or benzyl and X is H, phosphate, diphosphate or triphosphate

Fig. 3

New Acid cleavable Sieber linker (3)

Klenow exo- TMR dUTP
pH7.5

0 1 3 5 10 min.

AG t = 0, 1, 3, 5, 10

50mM Tris-HCl pH7.5, 10mM NaCl, 2mM DTT, 0.1mM EDTA
5mM MgCl2, 2uM dNTP-fluor, 100nM SHP 5T hairpin AG oligo,
Klenow exo- (Amersham-Joyce) 10units.

Fig. 5

SEQUENCE LISTING

```
<160> NUMBER OF SEQ ID NOS: 1

<210> SEQ ID NO 1
<211> LENGTH: 63
<212> TYPE: DNA
<213> ORGANISM: Artificial Sequence
<220> FEATURE:
<223> OTHER INFORMATION: Synthetic Oligonucleotide
<220> FEATURE:
<221> NAME/KEY: misc_feature
<222> LOCATION: 40
<223> OTHER INFORMATION: thymidine with an amino modification on the
      C6 position

<400> SEQUENCE: 1
taccgtcgac gtcgacgctg gcgagcgtgc tgcggttttt ttaccgcagc acgctcgcca    60
gcg                                                                 63
```

LABELLED NUCLEOTIDES

RELATED APPLICATIONS

This application is a Divisional Application of U.S. application Ser. No. 10/227,131, now U.S. Pat. No. 7,057,026 filed Aug. 23, 2002 which in turn claims benefit of United Kingdom Application No. GB0129012.1, filed Dec. 4, 2001. The entire teachings of the above applications are incorporated herein by reference.

FIELD OF THE INVENTION

This invention relates to labelled nucleotides. In particular, this invention discloses nucleotides having a removable label and their use in polynucleotide sequencing methods.

BACKGROUND

Advances in the study of molecules have been led, in part, by improvement in technologies used to characterise the molecules or their biological reactions. In particular, the study of the nucleic acids DNA and RNA has benefited from developing technologies used for sequence analysis and the study of hybridisation events.

An example of the technologies that have improved the study of nucleic acids, is the development of fabricated arrays of immobilised nucleic acids. These arrays consist typically of a high-density matrix of polynucleotides immobilised onto a solid support material. See, e.g., Fodor et al., *Trends Biotech.* 12:19-26, 1994, which describes ways of assembling the nucleic acids using a chemically sensitized glass surface protected by a mask, but exposed at defined areas to allow attachment of suitably modified nucleotide phosphoramidites. Fabricated arrays can also be manufactured by the technique of "spotting" known polynucleotides onto a solid support at predetermined positions (e.g., Stimpson et al., *Proc. Natl. Acad. Sci. USA* 92:6379-6383, 1995).

A further development in array technology is the attachment of the polynucleotides to the solid support material to form single molecule arrays. Arrays of this type are disclosed in International Patent App. WO 00/06770. The advantage of these arrays is that reactions can be monitored at the single molecule level and information on large numbers of single molecules can be collated from a single reaction.

For DNA arrays to be useful, the sequences of the molecules must be determined. U.S. Pat. No. 5,302,509 discloses a method to sequence polynucleotides immobilised on a solid support. The method relies on the incorporation of 3'-blocked bases A, G, C and T having a different fluorescent label to the immobilised polynucleotide, in the presence of DNA polymerase. The polymerase incorporates a base complementary to the target polynucleotide, but is prevented from further addition by the 3'-blocking group. The label of the incorporated base can then be determined and the blocking group removed by chemical cleavage to allow further polymerisation to occur.

Welch et al. (*Chem. Eur. J.* 5(3):951-960, 1999) describes the synthesis of nucleotide triphosphates modified with a 3'-O-blocking group that is photolabile and fluorescent. The modified nucleotides are intended for use in DNA sequencing experiments. However, these nucleotides proved to be difficult to incorporate onto an existing polynucleotide, due to an inability to fit into the polymerase enzyme active site.

Zhu et al. (*Cytometry* 28:206-211, 1997) also discloses the use of fluorescent labels attached to a nucleotide via the base group. The labelled nucleotides are intended for use in fluorescence in situ hybridisation (FISH) experiments, where a series of incorporated labelled nucleotides is required to produce a fluorescent "bar code".

SUMMARY OF THE INVENTION

In the present invention, a nucleoside or nucleotide molecule is linked to a detectable label via a cleavable linker group attached to the base, rendering the molecule useful in techniques using Labelled nucleosides or nucleotides, e.g., sequencing reactions, polynucleotide synthesis, nucleic acid amplification, nucleic acid hybridization assays, single nucleotide polymorphism studies, and other techniques using enzymes such as polymerases, reverse transcriptases, terminal transferases, or other DNA modifying enzymes. The invention is especially useful in techniques that use Labelled dNTPs, such as nick translation, random primer labeling, end-labeling (e.g., with terminal deoxynucleotidyltransferase), reverse transcription, or nucleic acid amplification. The molecules of the present invention are in contrast to the prior art, where the label is attached to the ribose or deoxyribose sugar, or where the label is attached via a non-cleavable linker.

According to a first aspect of the invention, a nucleotide or nucleoside molecule, or an analog thereof, has a base that is linked to a detectable label via a cleavable linker.

The invention features a nucleotide or nucleoside molecule, having a base that is linked to a detectable label via a cleavable linker. The base can be a purine, or a pyrimidine. The base can be a deazapurine. The molecule can have a ribose or deoxyribose sugar moiety. The ribose or deoxyribose sugar can include a protecting group attached via the 2' or 3' oxygen atom. The protecting group can be removed to expose a 3'-OH. The molecule can be a deoxyribonucleotide triphosphate. The detectable label can be a fluorophore. The linker can be an acid labile linker, a photolabile linker, or can contain a disulphide linkage.

The invention also features a method of labeling a nucleic acid molecule, where the method includes incorporating into the nucleic acid molecule a nucleotide or nucleoside molecule, where the nucleotide or nucleoside molecule has a base that is linked to a detectable label via a cleavable linker. The incorporating step can be accomplished via a terminal transferase, a polymerase or a reverse transcriptase. The base can be a purine, or a pyrimidine. The base can be a deazapurine. The nucleotide or nucleoside molecule can have a ribose or deoxyribose sugar moiety. The ribose or deoxyribose sugar can include a protecting group attached via the 2' or 3' oxygen atom. The protecting group can be removed to expose a 3'-OH group. The molecule can be a deoxyribonucleotide triphosphate. The detectable label can be a fluorophore. The linker can be an acid labile linker, a photolabile linker, or can contain a disulphide linkage. The detectable label and/or the cleavable linker can be of a size sufficient to prevent the incorporation of a second nucleotide or nucleoside into the nucleic acid molecule.

In another aspect, the invention features a method for determining the sequence of a target single-stranded polynucleotide, where the method includes monitoring the sequential incorporation of complementary nucleotides, where the nucleotides each have a base that is linked to a detectable label via a cleavable linker, and where the identity of each nucleotide incorporated is determined by detection of the label linked to the base, and subsequent removal of the label.

The invention also features a method for determining the sequence of a target single-stranded polynucleotide, where the method includes: (a) providing nucleotides, where the nucleotides have a base that is linked to a detectable label via a cleavable linker, and where the detectable label linked to each type of nucleotide can be distinguished upon detection from the detectable label used for other types of nucleotides; (b) incorporating a nucleotide into the complement of the target single stranded polynucleotide; (c) detecting the label of the nucleotide of (b), thereby determining the type of nucleotide incorporated; (d) removing the label of the nucleotide of (b); and (e) optionally repeating steps (b)-(d) one or more times; thereby determining the sequence of a target single-stranded polynucleotide.

In the methods described herein, each of the nucleotides can be brought into contact with the target sequentially, with removal of non-incorporated nucleotides prior to addition of the next nucleotide, where detection and removal of the label is carried out either after addition of each nucleotide, or after addition of all four nucleotides.

In the methods, all of the nucleotides can be brought into contact with the target simultaneously, i.e., a composition comprising all of the different nucleotides is brought into contact with the target, and non-incorporated nucleotides are removed prior to detection and subsequent to removal of the label(s).

The methods can comprise a first step and a second step, where in the first step, a first composition comprising two of the four nucleotides is brought into contact with the target, and non-incorporated nucleotides are removed prior to detection and subsequent to removal of the label, and where in the second step, a second composition comprising the two nucleotides not included in the first composition is brought into contact with the target, and non-incorporated nucleotides are removed prior to detection and subsequent to removal of the label, and where the first steps and the second step can be optionally repeated one or more times.

The methods described herein can also comprise a first step and a second step, where in the first step, a composition comprising one of the four nucleotides is brought into contact with the target, and non-incorporated nucleotides are removed prior to detection and subsequent to removal of the label, and where in the second step, a second composition. comprising the three nucleotides not included in the first composition is brought into contact with the target, and non-incorporated nucleotides are removed prior to detection and subsequent to removal of the label, and where the first steps and the second step can be optionally repeated one or more times.

The methods described herein can also comprise a first step and a second step, where in the first step, a first composition comprising three of the four nucleotides is brought into contact with the target, and non-incorporated nucleotides are removed prior to detection and subsequent to removal of the label, and where in the second step, a composition comprising the nucleotide not included in the first composition is brought into contact with the target, and non-incorporated nucleotides are removed prior to detection and subsequent to removal of the label, and where the first steps and the second step can be optionally repeated one or more times.

In a further aspect, the invention features a kit, where the kit includes: (a) individual the nucleotides, where each nucleotide has a base that is linked to a detectable label via a cleavable linker, and where the detectable label linked to each nucleotide can be distinguished upon detection from the detectable label used for other three nucleotides; and (b) packaging materials therefor. The kit can further include an enzyme and buffers appropriate for the action of the enzyme.

The nucleotides/nucleosides are suitable for use in many different DNA-based methodologies, including DNA synthesis and DNA sequencing protocols.

According to another aspect of the invention, a method for determining the sequence of a target polynucleotide comprises monitoring the sequential incorporation of complementary nucleotides, wherein the nucleotides comprise a detectable label linked to the base portion of the nucleotide via a cleavable linker, incorporation is detected by monitoring the label, and the label is removed to permit further nucleotide incorporation to occur.

DESCRIPTION OF THE DRAWINGS

FIG. 1 shows examplary nucleotide structures useful in the invention. For each structure, X can be H, phosphate, diphosphate or triphosphate. $R_1$ and $R_2$ can be the same or different, and can be selected from H, OH, or any group which can be transformed into an OH, including, but not limited to, a carbonyl. Some suitable functional groups for $R_1$ and $R_2$ include the structures shown in FIG. 3.

FIG. 3 shows some functional molecules useful in the invention, including some cleavable linkers and some suitable hydroxyl protecting groups. In these structures, $R_1$ and $R_2$ may be the same of different, and can be H, OH, or any group which can be transformed into an OH group, including a carbonyl. $R_3$ represents one or more substituents independently selected from alkyl, alkoxyl, amino or halogen groups. Alternatively, cleavable linkers may be constructed from any labile functionality used on the 3'-block. $R_4$ and $R_5$ can be H or alkyl, and $R_6$ can be alkyl, cycloalkyl, alkenyl, cycloalkenyl or benzyl. X can be H, phosphate, diphosphate or triphosphate.

FIG. 5 shows a denaturing gel showing the incorporation of the triphosphate of Example 3 using Klenow polymerase.

DETAILED DESCRIPTION

Figure 2:
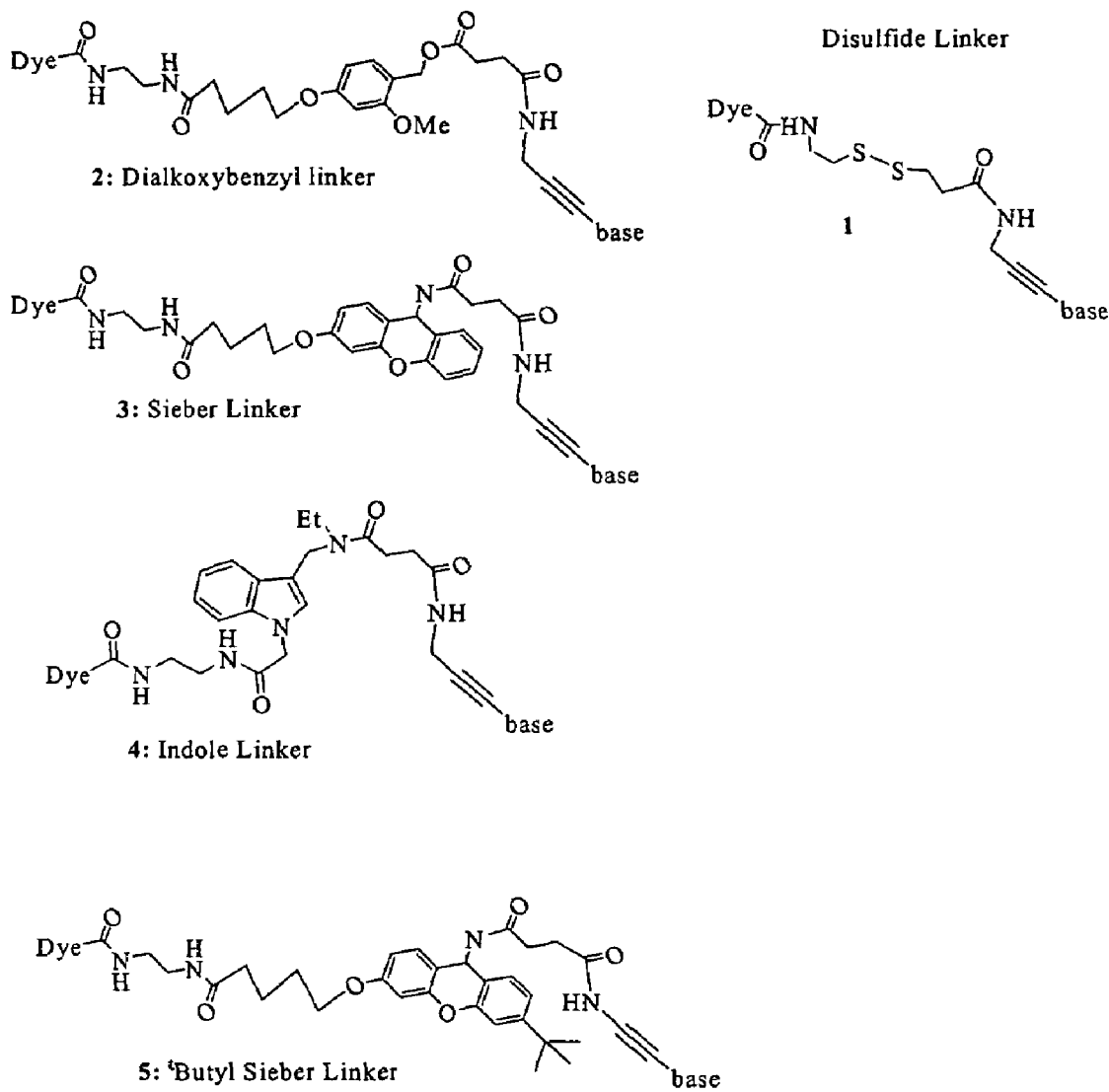
FIG. 2 shows structures of linkers useful in the invention, including (1) disulfide linkers and acid labile linkers, (2) dialkoxybenzyl linkers, (3) Sieber linkers, (4) indole linkers and (5) t-butyl Sieber linkers.

The present invention relates to nucleotides and nucleosides that are modified by attachment of a label via a cleavable linker, thereby rendering the molecule useful in techniques where the labelled molecule is to interact with an enzyme, such as sequencing reactions, polynucleotide synthesis, nucleic acid amplification, nucleic acid hybridization assays, single nucleotide polymorphism studies, techniques using enzymes such as polymerase, reverse transcriptase, terminal transferase, techniques that use Labelled dNTPs (e.g., nick translation, random primer labeling, end-labeling (e.g., with terminal deoxynucleotidyltransferase), reverse transcription, or nucleic acid amplification).

As is known in the art, a "nucleotide" consists of a nitrogenous base, a sugar, and one or more phosphate groups. In RNA, the sugar is a ribose, and in DNA is a deoxyribose, i. e., a sugar lacking a hydroxyl group that is present in ribose. The nitrogenous base is a derivative of purine or pyrimidine. The purines are adenosine (A) and guanidine (G), and the pyrimidines are cytidine (C) and thymidine (T) (or in the context of RNA, uracil (U)). The C-1 atom of deoxyribose is bonded to N-1 of a pyrimidine or N-9 of a purine. A nucleotide is also a phosphate ester of a nucleoside, with esterification occurring on the hydroxyl group attached to C-5 of the sugar. Nucleotides are usually mono, di- or triphosphates.

A "nucleoside" is structurally similar to a nucleotide, but are missing the phosphate moieties. An example of a nucleoside analog would be one in which the label is linked to the base and there is no phosphate group attached to the sugar molecule.

Although the base is usually referred to as a purine or pyrimidine, the skilled person will appreciate that derivatives and analogs are available which do not alter the capability of the nucleotide or nucleoside to undergo Watson-Crick base pairing. "Derivative" or "analog" means a compound or molecule whose core structure is the same as, or closely resembles that of, a parent compound, but which has a chemical or physical modification, such as a different or additional side groups, which allows the derivative nucleotide or nucleoside to be linked to another molecule. For example, the base can be a deazapurine. The derivatives should be capable of undergoing Watson-Crick pairing. "Deivative" and "analog" also mean a synthetic nucleotide or nucleoside derivative having modified base moieties and/or modified sugar moieties. Such derivatives and analogs are discussed in, e.g., Scheit, *Nucleotide Analogs* (John Wiley & Son, 1980) and Uhlman et al., *Chemical Reviews* 90:543-584, 1990. Nucleotide analogs can also comprise modified phosphodiester linkages, including phosphorothioate, phosphorodithioate, alkylphosphonate, phosphoranilidate and phosphoramidate linkages. The analogs should be capable of undergoing Watson-Crick base pairing. "Derivative" and "analog", as used herein, may be used interchangeably, and are encompassed by the terms "nucleotide" and "nucleoside" as defined herein.

The present invention can make use of conventional detectable labels. Detection can be carried out by any suitable method, including fluorescence spectroscopy or by other optical means. The preferred label is a fluorophore, which, after absorption of energy, emits radiation at a defined wavelength. Many suitable fluorescent labels are known. For example, Welch et al. (*Chem. Eur. J.* 5(3):951-960, 1999) discloses dansyl-functionalised fluorescent moieties that can be used in the present invention. Zhu et al. (*Cytometry* 28:206-211, 1997) describes the use of the fluorescent labels Cy3 and Cy5, which can also be used in the present invention. Labels suitable for use are also disclosed in Prober et al. (*Science* 238:336-341, 1987); Connell et al. (*BioTechniques* 5(4):342-384, 1987), Ansorge et al. (*Nucl. Acids Res.* 15(11): 4593-4602, 1987) and Smith et al. (*Nature* 321:674, 1986). Other commercially available fluorescent labels include, but are not limited to, fluorescein, rhodamine (including TMR, texas red and Rox), alexa, bodipy, acridine, coumarin, pyrene, benzanthracene and the cyanins.

Multiple labels can also be used in the invention. For example, bi-fluorophore FRET cassettes (*Tet. Letts.* 46:8867-8871, 2000) are well known in the art and can be utilised in the present invention. Multi-fluor dendrimeric systems (*J. Amer. Chem. Soc.* 123:8101-8108, 2001) can also be used.

Although fluorescent labels are preferred, other forms of detectable labels will be apparent as useful to those of ordinary skill. For example, microparticles, including quantum dots (Empodocles, et al., *Nature* 399:126-130, 1999), gold nanoparticles (Reichert et al., *Anal. Chem.* 72:6025-6029, 2000), microbeads (Lacoste et al., *Proc. Natl. Acad. Sci USA* 97(17):9461-9466, 2000), and tags detectable by mass spectrometry can all be used.

Multi-component labels can also be used in the invention. A multi-component label is one which is dependent on the interaction with a further compound for detection. The most common multi-component label used in biology is the biotin-streptavidin system. Biotin is used as the label attached to the nucleotide base. Streptavidin is then added separately to enable detection to occur. Other multi-component systems are available. For example, dinitrophenol has a commercially available fluorescent antibody that can be used for detection.

The label (or label and linker construct) can be of a size or structure sufficient to act as a block to the incorporation of a further nucleotide onto the nucleotide of the invention. This permits controlled polymerization to be carried out. The block can be due to steric hindrance, or can be due to a combination of size, charge and structure.

The invention will be further described with reference to nucleotides. However, unless indicated otherwise, the reference to nucleotides is also intended to be applicable to nucleosides. The invention will also be further described with reference to DNA, although the description will also be applicable to RNA, PNA, and other nucleic acids, unless otherwise indicated.

The modified nucleotides of the invention use a cleavable linker to attach the label to the nucleotide. The use of a cleavable linker ensures that the label can, if required, be removed after detection, avoiding any interfering signal with any labelled nucleotide incorporated subsequently.

Cleavable linkers are known in the art, and conventional chemistry can be applied to attach a linker to a nucleotide base and a label. The linker can be cleaved by any suitable method, including exposure to acids, bases, nucleophiles, electrophiles, radicals, metals, reducing or oxidising agents, light, temperature, enzymes etc. Suitable linkers can be adapted from standard chemical blocking groups, as disclosed in Greene & Wuts, *Protective Groups in Organic Synthesis*, John Wiley & Sons. Further suitable cleavable linkers used in solid-phase synthesis are disclosed in Guillier et al. (*Chem. Rev.* 100:2092-2157, 2000).

The use of the term "cleavable linker" is not meant to imply that the whole linker is required to be removed from the nucleotide base. The cleavage site can be located at a position on the linker that ensures that part of the linker remains attached to the nucleotide base after cleavage.

The linker can be attached at any position on the nucleotide base provided that Watson-Crick base pairing can still be carried out. In the context of purine bases, it is preferred if the linker is attached via the 7 position of the purine or the preferred deazapurine analogue, via an 8-modified purine, via an N-6 modified adenosine or an N-2 modified guanine. For pyrimidines, attachment is preferably via the 5 position on cytidine, thymidine or uracil and the N-4 position on cytosine. Suitable nucleotide structures are shown in FIG. 1. For each structure in FIG. 1, X can be H, phosphate, diphosphate or triphosphate. $R_1$ and $R_2$ can be the same or different, and can be selected from H, OH, or any group which can be transformed into an OH, including, but not limited to, a carbonyl. Some suitable functional groups for $R_1$ and $R_2$ include the structures shown in FIG. 3.

Suitable linkers are shown in FIG. 2 and include, but are not limited to, disulfide linkers (1), acid labile linkers (2, 3, 4 and 5; including dialkoxybenzyl linkers (e.g., 2), Sieber linkers (e.g., 3), indole linkers (e.g., 4), t-butyl Sieber linkers (e.g., 5)), electrophilically cleavable linkers, nucleophilically cleavable linkers, photocleavable linkers, cleavage under reductive conditions, oxidative conditions, cleavage via use of safety-catch linkers, and cleavage by elimination mechanisms.

A. Electrophilically Cleaved Linkers.

Electrophilically cleaved linkers are typically cleaved by protons and include cleavages sensitive to acids. Suitable linkers include the modified benzylic systems such as trityl, p-alkoxybenzyl esters and p-alkoxybenzyl amides. Other suitable linkers include tert-butyloxycarbonyl (Boc) groups and the acetal system (e.g., as is shown in FIG. 3 as O—C ($R_4$)($R_5$)—O—$R_6$.

The use of thiophilic metals, such as nickel, silver or mercury, in the cleavage of thioacetal or other sulphur-containing protecting groups can also be considered for the preparation of suitable linker molecules.

B. Nucleophilically Cleaved Linkers.

Nucleophilic cleavage is also a well recognised method in the preparation of linker molecules. Groups such as esters that are labile in water (i.e., can be cleaved simply at basic pH) and groups that are labile to non-aqueous nucleophiles, can be used. Fluoride ions can be used to cleave silicon-oxygen bonds in groups such as triisopropyl silane (TIPS) or t-butyldimethyl silane (TBDMS).

C. Photocleavable Linkers.

Photocleavable linkers have been used widely in carbohydrate chemistry. It is preferable that the light required to activate cleavage does not affect the other components of the modified nucleotides. For example, if a fluorophore is used as the label, it is preferable if this absorbs light of a different wavelength to that required to cleave the linker molecule. Suitable linkers include those based on O-nitrobenyl compounds and nitroveratryl compounds. Linkers based on benzoin chemistry can also be used (Lee et al., *J. Org. Chem.* 64:3454-3460, 1999).

D. Cleavage Under Reductive Conditions

There are many linkers known that are susceptible to reductive cleavage. Catalytic hydrogenation using palladium-based catalysts has been used to cleave benzyl and benzyloxycarbonyl groups. Disulphide bond reduction is also known in the art.

E. Cleavage Under Oxidative Conditions

Oxidation-based approaches are well known in the art. These include oxidation of p-alkoxybenzyl groups and the oxidation of sulphur and selenium linkers. The use of aqueous iodine to cleave disulphides and other sulphur or selenium-based linkers is also within the scope of the invention.

F. Safety-Catch Linkers

Safety-catch linkers are those that cleave in two steps. In a preferred system the first step is the generation of a reactive nucleophilic center followed by a second step involving an intra-molecular cyclization that results in cleavage. For example, levulinic ester linkages can be treated with hydrazine or photochemistry to release an active amine, which can then be cyclised to cleave an ester elsewhere in the molecule (Burgess et al., *J. Org. Chem.* 62:5165-5168, 1997).

G. Cleavage by Elimination Mechanisms

Elimination reactions can also be used. For example, the base-catalysed elimination of groups such as Fmoc and cyanoethyl, and palladium-catalysed reductive elimination of allylic systems, can be used.

As well as the cleavage site, the linker can comprise a spacer unit. The spacer distances the nucleotide base from the cleavage site or label. The length of the linker is unimportant provided that the label is held a sufficient distance from the nucleotide so as not to interfere with any interaction between the nucleotide and an enzyme.

The modified nucleotides can also comprise additional groups or modifications to the sugar group. For example, a dideoxyribose derivative, lacking two oxygens on the ribose ring structure (at the 2' and 3' positions), can be prepared and used as a block to further nucleotide incorporation on a growing oligonucleotide strand. The ribose ring can also be modified to include a protecting group at the 3' position or a group that can be transformed or modified to form a 3' OH group. The protecting group is intended to prevent nucleotide incorporation onto a nascent polynucleotide strand, and can be removed under defined conditions to allow polymerisation to occur. In contrast to the prior art, there is no detectable label attached at the ribose 3' position. This ensures that steric hindrance with the polymerase enzyme is reduced, while still allowing control of incorporation using the protecting group.

The skilled person will appreciate how to attach a suitable protecting group to the ribose ring to block interactions with the 3'-OH. The protecting group can be attached directly at the 3' position, or can be attached at the 2' position (the protecting group being of sufficient size or charge to block interactions at the 3' position). Alternatively, the protecting group can be attached at both the 3' and 2' positions, and can be cleaved to expose the 3' OH group.

Suitable protecting groups will be apparent to the skilled person, and can be formed from any suitable protecting group disclosed in Green and Wuts, supra. Some examples of such protecting groups are shown in FIG. 3. The protecting group should be removable (or modifiable) to produce a 3' OH group. The process used to obtain the 3' OH group can be any suitable chemical or enzymic reaction.

The labile linker may consist of functionality cleavable under identical conditions to the block. This will make the deprotection process more efficient as only a single treatment will be required to cleave both the label and the block. Thus the linker may contain functional groups as described in FIG. 3, which could be cleaved with the hydroxyl functionality on either the residual nucleoside or the removed label. The linker may also consist of entirely different chemical functionality that happens to be labile to the conditions used to cleave the block.

The term "alkyl" covers both straight chain and branched chain alkyl groups. Unless the context indicates otherwise, the term "alkyl" refers to groups having 1 to 8 carbon atoms, and typically from 1 to 6 carbon atoms, for example from 1 to 4 carbon atoms. Examples of alkyl groups include methyl, ethyl, propyl, isopropyl, n-butyl, isobutyl, tert-butyl, n-pentyl, 2-pentyl, 3-pentyl, 2-methyl butyl, 3-methyl butyl, and n-hexyl and its isomers.

Examples of cycloalkyl groups are those having from 3 to 10 ring atoms, particular examples including those derived from cyclopropane, cyclobutane, cyclopentane, cyclohexane and cycloheptane, bicycloheptane and decalin.

Examples of alkenyl groups include, but are not limited to, ethenyl (vinyl), 1-propenyl, 2-propenyl (allyl), isopropenyl, butenyl, buta-1,4-dienyl, pentenyl, and hexenyl.

Examples of cycloalkenyl groups include, but are not limited to, cyclopropenyl, cyclobutenyl, cyclopentenyl, cyclopentadienyl and cyclohexenyl.

The term alkoxy refers to $C_{1-6}$ alkoxy unless otherwise indicated: —OR, wherein R is a $C_{1-6}$ alkyl group. Examples of $C_{1-6}$ alkoxy groups include, but are not limited to, —OMe (methoxy), —OEt (ethoxy), —O(nPr) (n-propoxy), —O(iPr) (isopropoxy), —O(nBu) (n-butoxy), —O(sBu) (sec-butoxy), —O(iBu) (isobutoxy), and —O(tBu) (tert-butoxy).

The term amino refers to groups of type $NR^1R^2$, wherein $R^1$ and $R^2$ are independently selected from hydrogen, a $C_{1-6}$ alkyl group (also referred to as $C_{1-6}$ alkylamino or di-$C_{1-6}$ alkylamino).

The term "halogen" as used herein includes fluorine, chlorine, bromine and iodine.

The nucleotide molecules of the present invention are suitable for use in many different methods where the detection of nucleotides is required.

DNA sequencing methods, such as those outlined in U.S. Pat. No. 5,302,509 can be carried out using the nucleotides.

A method for determining the sequence of a target polynucleotide can be carried out by contacting the target polynucleotide separately with the different nucleotides to form the complement to that of the target polynucleotide, and detecting the incorporation of the nucleotides. Such a method makes use of polymerisation, whereby a polymerase enzyme extends the complementary strand by incorporating the correct nucleotide complementary to that on the target. The polymerisation reaction also requires a specific primer to initiate polymerisation.

For each cycle, the incorporation of the labelled nucleotide is carried out by the polymerase enzyme, and the incorporation event is then determined. Many different polymerase enzymes exist, and it will be evident to the person of ordinary skill which is most appropriate to use. Preferred enzymes include DNA polymerase I, the Klenow fragment, DNA polymerase III, T4 or T7 DNA polymerase, Taq polymerase or vent polymerase. A polymerase engineered to have specific properties can also be used.

The sequencing methods are preferably carried out with the target polynucleotide arrayed on a solid support. Multiple target polynucleotides can be immobilised on the solid support through linker molecules, or can be attached to particles, e.g., microspheres, which can also be attached to a solid support material.

The polynucleotides can be attached to the solid support by a number of means, including the use of biotin-avidin interactions. Methods for immobilizing polynucleotides on a solid support are well known in the art, and include lithographic techniques and "spotting" individual polynucleotides in defined positions on a solid support. Suitable solid supports are known in the art, and include glass slides and beads, ceramic and silicon surfaces and plastic materials. The support is usually a flat surface although microscopic beads (microspheres) can also be used and can in turn be attached to another solid support by known means. The microspheres can be of any suitable size, typically in the range of from 10 nm to 100 nm in diameter. In a preferred embodiment, the polynucleotides are attached directly onto a planar surface, preferably a planar glass surface. Attachment will preferably be by means of a covalent linkage. Preferably, the arrays that are used are single molecule arrays that comprise polynucleotides in distinct optically resolvable areas, e.g., as disclosed in International App. No. WO 00/06770.

The sequencing method can be carried out on both single polynucleotide molecule and multi-polynucleotide molecule arrays, i.e., arrays of distinct individual polynucleotide molecules and arrays of distinct regions comprising multiple copies of one individual polynucleotide molecule. Single molecule arrays allow each individual polynucleotide to be resolved separately. The use of single molecule arrays is preferred. Sequencing single molecule arrays non-destructively allows a spatially addressable array to be formed.

The method makes use of the polymerisation reaction to generate the complementary sequence of the target. The conditions necessary for polymerisation to occur will be apparent to the skilled person.

To carry out the polymerase reaction it will usually be necessary to first anneal a primer sequence to the target polynucleotide, the primer sequence being recognised by the polymerase enzyme and acting as an initiation site for the subsequent extension of the complementary strand. The primer sequence may be added as a separate component with respect to the target polynucleotide. Alternatively, the primer and the target polynucleotide may each be part of one single stranded molecule, with the primer portion forming an intramolecular duplex with a part of the target, i.e., a hairpin loop structure. This structure may be immobilised to the solid support at any point on the molecule. Other conditions necessary for carrying out the polymerase reaction, including temperature, pH, buffer compositions etc., will be apparent to those skilled in the art.

The modified nucleotides of the invention are then brought into contact with the target polynucleotide, to allow polymerisation to occur. The nucleotides may be added sequentially, i.e., separate addition of each nucleotide type (A, T, G or C), or added together. If they are added together, it is preferable for each nucleotide type to be labelled with a different label.

This polymerisation step is allowed to proceed for a time sufficient to allow incorporation of a nucleotide.

Nucleotides that are not incorporated are then removed, for example, by subjecting the array to a washing step, and detection of the incorporated labels may then be carried out.

Detection may be by conventional means, for example if the label is a fluorescent moiety, detection of an incorporated base may be carried out by using a confocal scanning microscope to scan the surface of the array with a laser, to image a fluorophore bound directly to the incorporated base. Alternatively, a sensitive 2-D detector, such as a charge-coupled detector (CCD), can be used to visualise the individual signals generated. However, other techniques such as scanning near-field optical microscopy (SNOM) are available and may be used when imaging dense arrays. For example, using SNOM, individual polynucleotides may be distinguished when separated by a distance of less than 100 nm, e.g., 10 nm to 10 μm. For a description of scanning near-field optical microscopy, see Moyer et al., *Laser Focus World* 29:10, 1993. Suitable apparatus used for imaging polynucleotide arrays are known and the technical set-up will be apparent to the skilled person.

After detection, the label may be removed using suitable conditions that cleave the linker.

The use of the modified nucleotides is not limited to DNA sequencing techniques, and other techniques, including polynucleotide synthesis, DNA hybridisation assays and single nucleotide polymorphism studies, may also be carried out using nucleotides of the invention. Any technique that involves the interaction between a nucleotide and an enzyme may make use of the molecules of the invention. For example, the molecule may be used as a substrate for a reverse transcriptase or terminal transferase enzyme.

Suitable structures are described in the following Examples and are shown in the accompanying drawings.

EXAMPLES

Example 1

Synthesis of Disulfide Linker

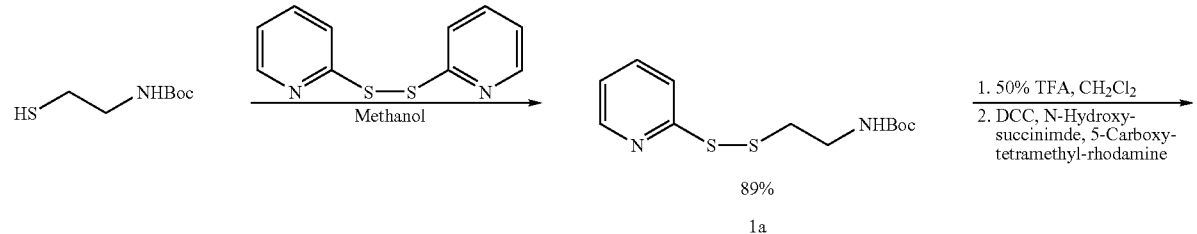

1a

-continued
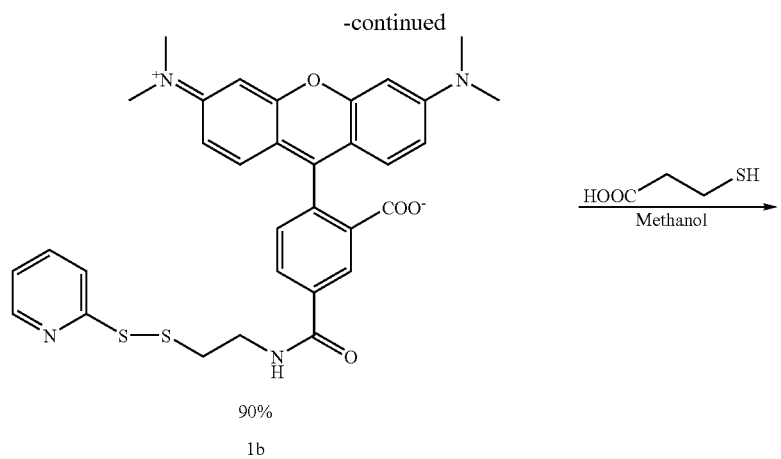
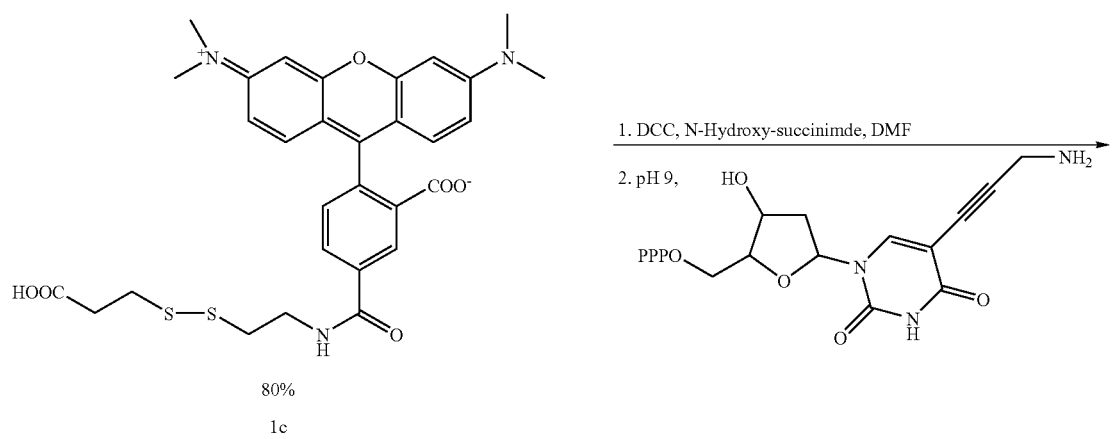
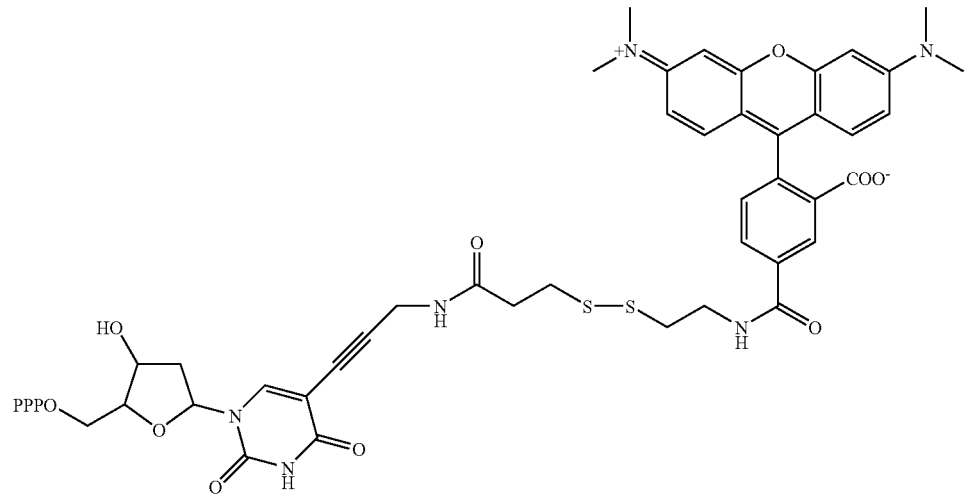

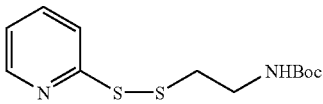

1a tButyl-N-(2-mercaptoethyl) carbamate (3 mmol, 0.5 mL) was added dropwise to a solution of 1.32 g (6.0 mmol) aldrithiol in 15 mL MeOH. After 1.5 h the reaction had gone to completion and the solvent was evaporated. The crude product was purified by chromatography on silica with ethyl acetate:petroleum ether (1:4). Product 1a was obtained as a slightly yellow oil (0.76 g, 2.67 mmol, 89%). $^1$H NMR (500 Mhz, $D_6$-DMSO): δ=1.38 (s, 9 H, tBu), 2.88 (t, J=6.6 Hz, 2 H, $SCH_2$) 3.20 (q, J=6.6 Hz, 2 H, $CH_2$NH), 7.02 (bs, 1 H, NH), 7.24 (ddd, J=7.3 Hz, J=4.9 Hz, J=1.0Hz, 1 H, H-5), 7.77 (dt, J=8.1 Hz, J=1.0 Hz, 1 H, H-3), 7.82 (ddd, J=8.1 Hz, J=7.4 Hz, J=1.8 Hz, 1 H, H-4), 8.46 (ddd, J=4.9 Hz, J=1.8 Hz, J=1.0 Hz, 1 H, H-6).

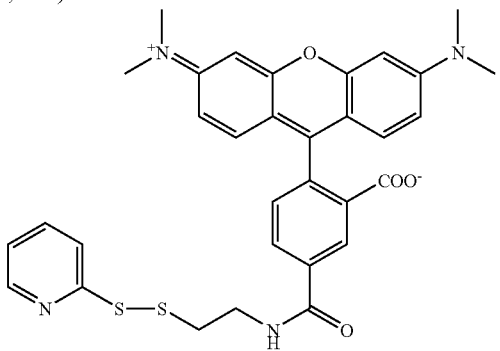

1b

To deprotect the amine of 1a, 17 mg of 1a (60 μmol) was dissolved in a mixture of 0.5 mL DCM and 0.5 mL trifluoracetic acid. This mixture was stirred for 2.5 h at rt and then the solvents were removed under reduced pressure. The residue was three times redissolved in 2 mL DCM and evaporated to dryness. The deprotected product was dried under high vacuum for 3 h and then dissolved in 1 mL dry DMF. It was assumed that the deprotection had gone to completion.

To a solution of 15 mg 5-carboxy tetra methyl rhodamine (35 μmol) in 2 mL DMF were added 8.0 mg N-hydroxy succinimide (70 μmol) and 7.8 mg DCC (38 μmol). The mixture was stirred for 6 h in the dark. Then 22 μl DIPEA (126 μmol) and the solution of deprotected 1a in 1 mL DMF were added. After stirring the reaction mixture overnight in the dark, the solvent was removed under reduced pressure. The residue was dissolved in DCM and washed with saturated NaCl solution. After drying over $MgSO_4$ the crude mixture was purified on silica with $CHCl_3$:MeOH (3:1) as solvent. 1b was isolated as a dark red solid in 90% yield (19.2 mg, 31.4 μmol). $^1$H NMR (500 MHz, $D_6$-DMSO): δ=3.09 (t, J=6.7 Hz, 2 H, $SCH_2$), 3.63 (q, J=6.2 Hz, 2 H, $CH_2$NH), 6.48-6.53 (m, 6 H, H-Anthracene), 7.23-7.26 [m, 1 H, H-5 (pyridine)], 7.32 (d, J=7.9 Hz, 1 Hz, H-3), 7.81-7.82 [m, 2 H, H-3+H-4 (pyridine)], 8.21 (d, J=7.9 Hz, 1 H, H-4), 8.43 (s, 1 H, H-6), 8.47 [dt, J=4.7 Hz, J=1.3 Hz, 1 H, H-6 (pyridine)], 9.03 (t, J=5.2 Hz, 1 H, NH).

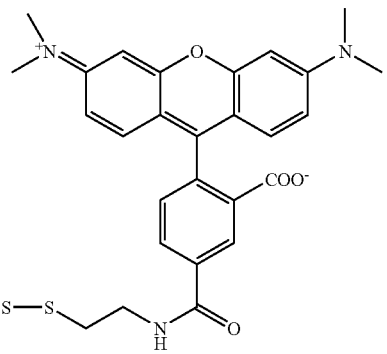

1c

Mercaptopropionic acid (20.6 μmol, 1.8 μl) was added to a solution of 19.6 mg 1b (32.7 μmol) in 2 mL MeOH. The mixture was stirred for 2.5 h in the dark. The solvent was removed under reduced pressure. The crude product was purified by chromatography on silica with $CHCl_3$:MeOH:AcOH 15:1:0.5 as the solvent mixture. 15.5 mg (26 μmol, 80%) dark red crystals 1c could be isolated. $^1$H NMR (500 MHz, $D_2O$): δ=2.53 (t, J=7.0 Hz, 2 H, $CH_2$COOH), 2.88 (t, J=7.0 Hz, 2 H, $CH_2CH_2$COOH), 2.96-2.99 (m, 2 H, $CH_2CH_2$NH), 3.73 (t, J=6.3 Hz, 2 H, $CH_2$NH), 6.53 (d, J=2.4 Hz, 2 H, H-Anthracene), 6.81 (dd, J=9.5 Hz, J=4.5 Hz, 2 H, H-Anthracene), 7.12 (d, J=9.5 Hz, 2 H, H-Anthracene), 7.48 (d, J=7.9 Hz, 1 H, H-3), 7.95 (dd, J=8.1 Hz, J=1.9 Hz, 1 H, H-2) 8.13 (d, J=1.9 Hz, 1 H, H-1). +ve electro spray ($C_{30}H_{31}N_3O_6S_2$): expected 593.17; found 594.3 [M+H], 616.2 [M+Na].

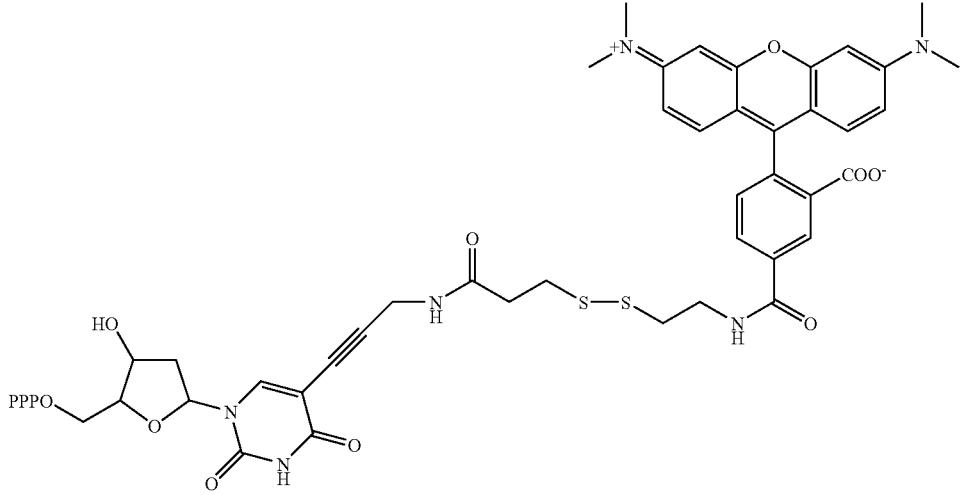

1

To a solution of 25.8 mg 1c (43.4 µmol) in 3 mL DMF (dry) were added 9.9 mg N-hydroxy succinimide (86.8 µmol) and 9.7 mg DCC (47.1 µmol). The mixture was stirred in the dark for 5 h at room temperature and then put in the fridge overnight. The mixture was filtered through a plug of cotton wool in a new flask and to this was added a solution of 865 µl propargylamino dUTP (14.7 µmol, 17 µmol in 1 mL H$_2$O) and 3 mL sodium borate buffer (0.1 M solution, pH 9). The mixture was stirred overnight. After removal of solvents the residue was dissolved in as little water as possible and purified by HPLC. A Zorbax C18 column was used with 0.1 M triethyl ammonium bicarbonate (TEAB) and acetonitrile as buffers. $^{31}$P NMR (400 MHz, D$_2$O): δ=−4.73 (d), −9.93 (d), 19.03 (t). -ve electro spray (C$_{42}$H$_{47}$N$_6$O$_{19}$P$_3$S$_2$ assuming 4 H$^+$ counter ions): expected 1096.16; found 1092.9. UV in Water: λ$_{(max)}$=555 nm A$_{(555)}$=0.885 (c=0.036 µmol).

Triphosphate (1) was successfully incorporated using Klenow DNA polymerase. The reaction was performed in the following conditions: 50 mM Tris.HCl (pH 7.5), 10 mM NaCl, 2 mM DTT, 0.1 mM EDTA, 5 mM MgCl$_2$, 2 µM compound 3, 100 nM DNA template (previously labelled with P32 and T4 polynucleotide kinase) and 10 units of commercial exo-Klenow (Amersham Corp., Arlington Heights, Ill., USA). The DNA templates were self-complementary hairpins (5'-TACCgTCgACgTCgACgCTggCgAgCgTgCTgCggTTTTT(C6-amino)TTACCgCAgCACgCTCgC-CAgCg; SEQ ID NO: 1). The reaction was performed in 100 µL volume at 37° C. with timepoints taken at 0, 1, 3, 5 and 10 min. The reaction products were electrophoresed down a denaturing (8 M urea) 20% polyacrylamide gel and imaged on a typhoon phosphorimager. Complete single base extension was seen in 1 minute indicating efficient polymerase incorporation (disulfide linker gel, FIG. 3). A second set of lanes is shown in which the material is exposed to DTT after the incorporation. A different band shift can be seen which shows removal of the dye from the DNA construct, thus a cycle of polymerase incorporation and cleavage has been shown using this disulfide compound.

Example 2

Synthesis of TMR-Sieber Linker Free Acid

5-[-9-[9-(fluorenyl-methyloxycarbonyl)amino]xanthen-3-yl]valeric acid, (42.8 mg, 80 µmol) was stirred at room temperature with disuccinimidyl carbonate (22.5 mg, 88 µmol) and N,N-dimethyl aminopyridine (10.8 mg, 88 µmol) in DMF. After 5 minutes, mono-5-carboxy TMR ethylene diamine (198.9 mg, 40 µmol) was added followed by DIPEA (13.9 µl, 80 µmol). The reaction was stirred at room temperature. After 2 hrs, the reaction mixture was diluted with dichloromethane (100 mL) and the resulting solution was extracted with 1 M aqueous potassium dihydrogen phosphate (50 mL). The DCM layer was separated and evaporated under reduced pressure. The residue was purified by a short column chromatography. The fractions eluting with 40% methanol in chloroform were collected and evaporated under reduced pressure. The residue was then dissolved in dry DMF (1 mL) and N-(2-mercaptoethyl)aminomethyl polystyrene (200 mg, 400 µmol) and DBU (12 µl, 80 µmol). After 10 minutes at room temperature, the resins were filtered off and rinsed with dry DMF (1 mL). All the filtrates were combined and then added to a solution of succinic anhydride (80 mg, 800 µmol), DIPEA (139 µl, 800 µmol) and DMAP (9.8 mg, 80 µmol) in DMF (1 mL). The reaction mixture was then stirred at room temperature. After overnight (16 hrs), all the solvents were evaporated under reduced pressure and the residue was purified by a short column chromatography. The title compound eluted with 30% methanol in chloroform was obtained as purple powders (22 mg, overall yield 63%). $^1$HNMR [D$_6$-DMSO]: 8.82 (1H, t, J 5.4, ex.), 8.75 (1H, d, J 8.9, ex.), 8.42 (1H, d, J 1.5), 8.20 (1H, dd, J 8.0 and 1.5), 7.95 (1H, t, J 5.9, ex.), 7.34 (1H, d, J 7.3), 7.30-7.27 (2H, m), 7.21 (1H, d, J 8.5), 7.16-7.07 (2H, m), 6.68 (1H, dd, J 8.8 and 2.5), 6.65 (1H, d, J 2.4), 6.49-6.43 (6H, m), 6.18 (1H, d, J 5.6), 3.95 (1H, t, J 5.9), 3.39-3.36 (2H, m), 3.30-3.27 (2H, m), 2.92 (12H, s), 2.37-2.33 (2H, m), 2.14(2H, t, J 7.2) and 1.70-1.62 (4H, m). MS[(ES(+)], m/z 868.5 (MH$^+$).

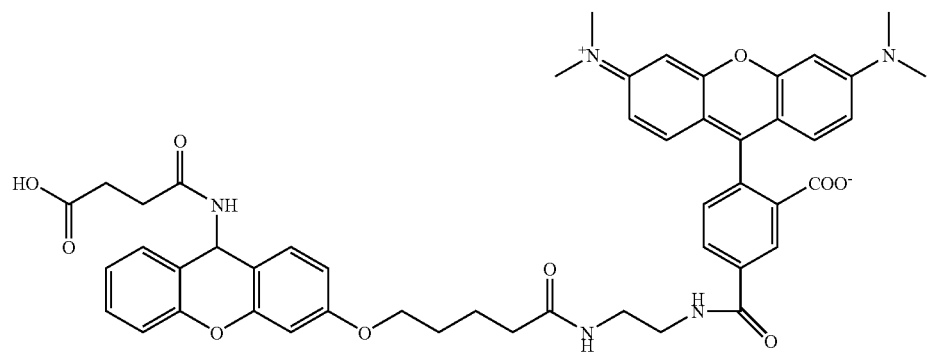

Example 3

Synthesis of TMR-Sieber Linker-dUTP (3)

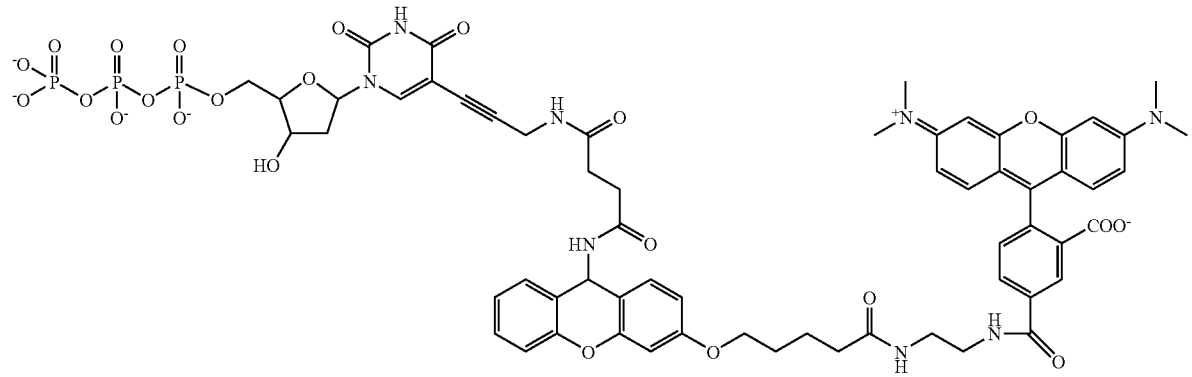

TMR-sieber linker free acid (4.34 mg, 5 µmol) was stirred with disuccinimidyl carbonate (1.74 mg, 7.5 µmol) and N,N-dimethyl aminopyridine (0.92 mg, 7.5 µmol) in DMF (1 mL) at room temperature. After 10 minutes, all the reaction mixture was added to tetra-(tri-butylammonium) salt of 5-(3-aminopropynyl)-2'-deoxyuridine-5'-triphosphate (10 µmol). The reaction was stirred at room temperature for 4 hrs and stored in the fridge overnight. The reaction mixture was then diluted with chilled water (10 mL) and all the resulting solution was applied onto a short column of DEAE A-25. The column was initially eluted with 0.1 M TEAB buffer and then 0.7 M TEAB buffer. The 0.7 M TEAB eluents were collected and evaporated under reduced pressure. The residue was co-evaporated with MeOH (2×10 mL) and then purified by preparative HPLC. The title compound was obtained as triethylammonium salt in 31% yield (based on the quantification of TMR at 555 nm in water (pH 7)). $^1$HNMR in D$_2$O indicated two diastereoisomers, due to the sieber linker moiety and there were approximately three triethylammonium count ions. $^1$HNMR [D$_2$O]: 8.18 (1H, m), 8.06 (1H, m), 7.76 (0.55H, s), 7.74 (0.45H, s), 7.36-7.09 (5H, m), 6.89-6.72 (3H, m), 6.59-6.37 (5H, m), 6.12 (0.55H, t, J 6.6), 6.05 (0.45H, t, J 6.6), 5.99 (0.45H, d, J 2.5), 5.91 (1.1H, m), 5.88 (0.45H, s), 4.49 (0.55H, m), 4.43 (0.45H, m), 4.00-3.35 (9H, m), 3.30-2.95 (32H, m), 2.65-2.52 (4H, m), 2.25-2.05 (4H, m), 1.62-1.42 (4H, m) and 1.23 (27H, t, J 7.3). $^{31}$P [D$_2$O]: −9.91 ($^\gamma$P, d, J 19.2), [−11.08($^\alpha$P, d, J20.1) and −11.30 ($^\alpha$P, d, J 20.1), due to two diastereoisomers] and −22.57 ($^\beta$P, m). MS[(ES(−)], m/z 1369.1 (M$^-$).

Figure 4:
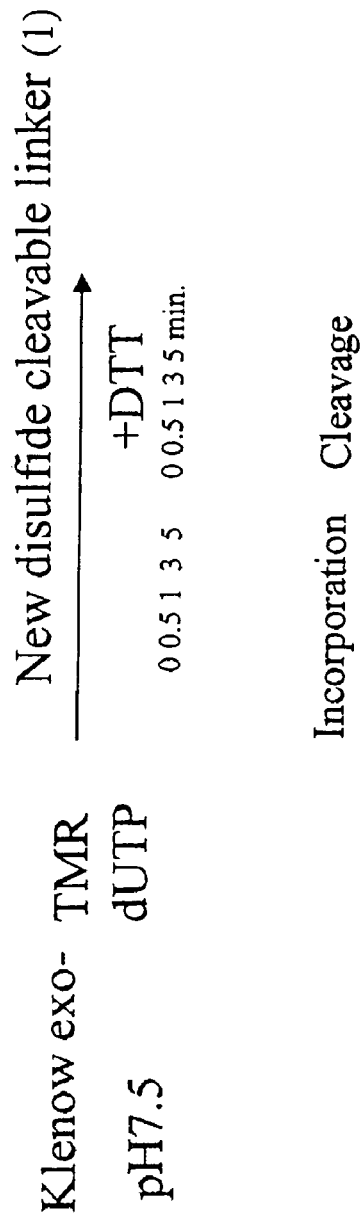
FIG. 4 shows a denaturing gel showing the incorporation of the triphosphate of Example 1 using Klenow polymerase.
Figure 6:
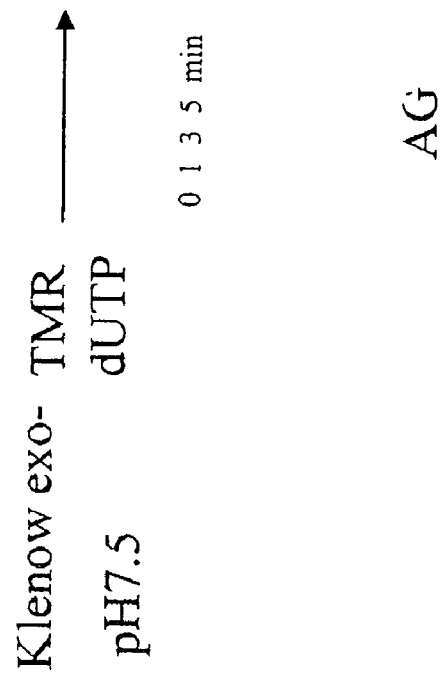
FIG. 6 shows a denaturing gel showing the incorporation of the triphosphate of Example 4 using Klenow polymerase.

Triphosphate (3) was successfully incorporated using Klenow DNA polymerase. The reaction was performed in the following conditions: 50 mM Tris.HCl (pH 7.5), 10 mM NaCl, 2 mM DTT, 0.1 mM EDTA, 5 mM MgCl$_2$, 2 µM compound 3, 100 nM DNA template (previously labelled with P32 and T4 polynucleotide kinase) and 10 units of commercial exo-Klenow (Amersham Corp. Arlington Heights, Illinois, USA). The DNA templates were self-complementary hairpins (5'-TACCgTCgACgTCgACgCTggCgAgCgT-gCTgCggTTTTT(C6-amino)TTACCgCAgCACgCTCgC-CAgCg; SEQ ID NO:1). The reaction was performed in 100 µL volume at 37° C. with timepoints taken at 0, 1, 3, 5 and 10 min. The reaction products were electrophoresed down a denaturing (8 M urea) 20% polyacrylamide gel and imaged on a typhoon phosphorimager. Complete single base extension was seen in 1 minute indicating efficient polymerase incorporation (Sieber linker gel, FIG. 4).

Example 4

Synthesis of TMR-Indole Linker-dUTP (4)

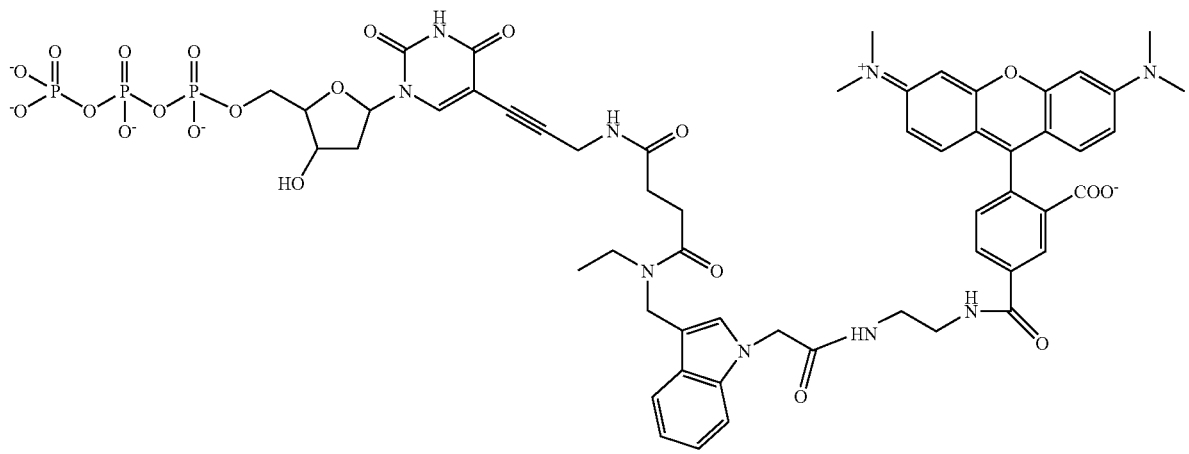

Triphosphate (4) was successfully incorporated using Klenow DNA polymerase. The reaction was performed in the following conditions: 50 mM Tris.HCl (pH 7.5), 10 mM NaCl, 2 mM DTT, 0.1 mM EDTA, 5 mM MgCl$_2$, 2 µM compound 3, 100 nM DNA template (previously labelled with P32 and T4 polynucleotide kinase) and 10 units of commercial exo-Klenow (Amersham Corp., Arlington Heights, Ill., USA). The DNA templates were self-complementary hairpins (5'-TACCgTCgACgTCgACgCTggCgAgCgTgCTgCggTTTTT(C6-amino)TTACCgCAgCACgCTCgC-CAgCg; SEQ ID NO:1). The reaction was performed in 100 µL volume at 37° C. with timepoints taken at 0, 1, 3, 5 and 10 min. The reaction products were electrophoresed down a denaturing (8 M urea) 20% polyacrylamide gel and imaged on a typhoon phosphorimager. Complete single base extension was seen in 1 minute indicating efficient polymerase incorporation (indole linker gel, FIG. 5).

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A method of labeling a nucleic acid molecule, the method comprising incorporating into the nucleic acid molecule a nucleotide or nucleoside molecule, wherein the nucleotide or nucleoside molecule has a base that is linked to a detectable label via a cleavable linker and the nucleotide or nucleoside molecule has a ribose or deoxyribose sugar moiety, wherein the ribose or deoxyribose sugar moiety comprises a protecting group attached via the 2' or 3' oxygen atom, and said protecting group can be modified or removed to expose a 3' OH group and the protecting group comprises an azido group.

2. The method of claim 1, wherein said incorporating is accomplished via a terminal transferase, a polymerase or a reverse transcriptase.

3. The method of claim 1, wherein the base is a deazapurine.

4. The method of claim 1, wherein the nucleotide is a deoxyribonucleotide triphosphate.

5. The method of claim 1, wherein the label is a fluorophore.

6. The method according to claim 1, wherein the protecting group is $CH_2N_3$.

7. A method of labeling a nucleic acid molecule, the method comprising incorporating into the nucleic acid molecule a nucleotide or nucleoside molecule, wherein the nucleotide or nucleoside molecule has a base that is linked to a detectable label via a cleavable linker and the nucleotide or nucleoside molecule has a ribose or deoxyribose sugar moiety, wherein the ribose or deoxyribose sugar moiety comprises a protecting group attached via the 2' or 3' oxygen atom, and said protecting group can be modified or removed to expose a 3' OH group and the protecting group and cleavable linker are removable under identical conditions.

8. The method according to claim 1, further comprising detecting the detectable label and cleaving the cleavable linker.

9. A method of labeling a nucleic acid molecule, the method comprising:
   a) incorporating into the nucleic acid molecule a nucleotide or nucleoside molecule, wherein the nucleotide or nucleoside molecule has a base that is linked to a detectable label via a cleavable linker, wherein the nucleotide or nucleoside molecule has a ribose or deoxyribose sugar moiety that comprises a protecting group attached via the 2' or 3' oxygen atom, and said protecting group can be modified or removed to expose a 3' OH group and the protecting group comprises an azido group;
   b) detecting the detectable label and cleaving the cleavable linker, wherein the protected hydroxyl functionality and the protecting group are cleavable under identical conditions; and
   c) repeating steps a) and b) at least once.

10. The method according to claim 7, wherein the cleavable linker and the protecting group both comprise an allyl moiety.

11. The method of claim 7, wherein said incorporating is accomplished via a terminal transferase, a polymerase or a reverse transcriptase.

12. The method of claim 7, wherein the base is a deazapurine.

13. The method of claim 7, wherein the nucleotide is a deoxyribonucleotide triphosphate.

14. The method of claim 7, wherein the label is a fluorophore.

15. A method of labeling a nucleic acid molecule, the method comprising:
a) incorporating into the nucleic acid molecule a nucleotide or nucleoside molecule, wherein the nucleotide or nucleoside molecule has a base that is linked to a detectable label via a cleavable linker, wherein the nucleotide or nucleoside molecule has a ribose or deoxyribose sugar moiety that comprises a protecting group attached via the 2' or 3' oxygen atom, and said protecting group can be modified or removed to expose a 3' OH group and the protecting group comprises an allyl moiety;
b) detecting the detectable label and cleaving the cleavable linker, wherein the protected hydroxyl functionality and the protecting group are cleavable under identical conditions; and
c) repeating steps a) and b) at least once.

* * * * *

(12) INTER PARTES REVIEW CERTIFICATE (25th)
United States Patent
Barnes et al.

(10) Number: US 7,566,537 K1
(45) Certificate Issued: Sep. 8, 2014

(54) LABELLED NUCLEOTIDES

(75) Inventors: Colin Barnes; Shankar Balasubramanian; Xiaohai Liu; Harold Swerdlow; John Milton; Xiaolin Wu

(73) Assignee: Illumina Cambridge Limited

Trial Number:
　　IPR2013-00518 filed Aug. 19, 2013

Petitioner: Intelligent Bio-Systems, Inc.

Patent Owner: Illumina Cambridge Ltd.

Inter Partes Review Certificate for:
　　Patent No.: 7,566,537
　　Issued: Jul. 28, 2009
　　Appl. No.: 11/301,578
　　Filed: Dec. 13, 2005

The results of IPR2013-00518 are reflected in this inter partes review certificate under 35 U.S.C. 318(b).

INTER PARTES REVIEW CERTIFICATE
U.S. Patent 7,566,537 K1
Trial No. IPR2013-00518
Certificate Issued Sep. 8, 2014

AS A RESULT OF THE INTER PARTES REVIEW PROCEEDING, IT HAS BEEN DETERMINED THAT:

Claims 7 and 11-14 are cancelled.

\* \* \* \* \*

(12) INTER PARTES REVIEW CERTIFICATE (2274th)
United States Patent
Barnes et al.

(10) Number: US 7,566,537 K2
(45) Certificate Issued: Aug. 17, 2021

(54) LABELLED NUCLEOTIDES

(75) Inventors: Colin Barnes; Shankar Balasubramanian; Xiaohai Liu; John Milton; Xiaolin Wu; Harold Swerdlow

(73) Assignee: ILLUMINA CAMBRIDGE LIMITED

Trial Number:

IPR2013-00517 filed Aug. 19, 2013

Inter Partes Review Certificate for:

Patent No.: 7,566,537
Issued: Jul. 28, 2009
Appl. No.: 11/301,578
Filed: Dec. 13, 2005

The results of IPR2013-00517 are reflected in this inter partes review certificate under 35 U.S.C. 318(b).

INTER PARTES REVIEW CERTIFICATE
U.S. Patent 7,566,537 K2
Trial No. IPR2013-00517
Certificate Issued Aug. 17, 2021

AS A RESULT OF THE INTER PARTES REVIEW PROCEEDING, IT HAS BEEN DETERMINED THAT:

Claims 1-6 and 8 are found patentable.

\* \* \* \* \*